US012766125B2

(12) United States Patent
Vashist et al.

(10) Patent No.: US 12,766,125 B2
(45) **Date of Patent: *Oct. 20, 2026**

(54) TREATMENT AND PREVENTION OF INFECTIONS USING VEGETABLE OIL-DERIVED POLYOLS

(71) Applicants: Arti Vashist, Miami, FL (US); Prem Chapagain, Miami, FL (US); Andrea Raymond, Miramar, FL (US); Hitendra Chand, Doral, FL (US); Madhavan Nair, Coral Gables, FL (US)

(72) Inventors: Arti Vashist, Miami, FL (US); Prem Chapagain, Miami, FL (US); Andrea Raymond, Miramar, FL (US); Hitendra Chand, Doral, FL (US); Madhavan Nair, Coral Gables, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/323,352

(22) Filed: Sep. 9, 2025

(65) Prior Publication Data

US 2026/0007628 A1 Jan. 8, 2026

Related U.S. Application Data

(63) Continuation of application No. 18/078,414, filed on Dec. 9, 2022, now Pat. No. 12,440,467.

(60) Provisional application No. 63/287,658, filed on Dec. 9, 2021.

(51) Int. Cl.
*A61K 31/231* (2006.01)
*A61P 31/14* (2006.01)

(52) U.S. Cl.
CPC ............ *A61K 31/231* (2013.01); *A61P 31/14* (2018.01)

(58) Field of Classification Search
CPC .............................. A61K 31/231; A61P 31/14
See application file for complete search history.

(56) References Cited

U.S. PATENT DOCUMENTS

| | | | | |
|---|---|---|---|---|
| 6,664,406 B1 * | 12/2003 | Coupland ............ | A61K 31/231 554/225 |
| 8,987,468 B2 * | 3/2015 | Wang ..................... | A61K 45/06 560/312 |
| 8,987,486 B2 | 3/2015 | Iinuma et al. | |
| 9,000,042 B2 * | 4/2015 | Escriba Ruiz ....... | A61K 31/185 514/560 |
| 10,344,100 B1 | 7/2019 | Vashist et al. | |
| 2020/0383932 A1 * | 12/2020 | Nair ..................... | A61K 9/5042 |
| 2022/0313617 A1 | 10/2022 | Nair et al. | |

FOREIGN PATENT DOCUMENTS

WO 2020/247730 A1 12/2020

OTHER PUBLICATIONS

Vashist, Arti, et al. "Development of multifunctional biopolymeric auto-fluorescent micro-and nanogels as a platform for biomedical applications." Frontiers in Bioengineering and Biotechnology 8 (2020): 315. (Year: 2020).*
Landovitz, Raphael J., Hyman Scott, and Steven G. Deeks. "Prevention, treatment and cure of HIV infection." Nature Reviews Microbiology 21.10 (2023): 657-670. (Year: 2023).*
Este, Jose A., and Tomas Cihlar. "Current status and challenges of antiretroviral research and therapy." Antiviral research 85.1 (2010): 25-33. (Year: 2010).*
Cava, Claudia, and Isabella Castiglioni. "Integration of molecular docking and in vitro studies: A powerful approach for drug discovery in breast cancer." Applied Sciences 10.19 (2020): 6981. (Year: 2020).*
Alli, Sema et al. "Castor oil-based graft copolymers: synthesis, characterization antimicrobial activity and antiproliferative effects against breast cancer cell lines." Polymer Bulletin 79: 11177-11199, Jan. 14, 2022.
Cava, Claudia and Isabella Castiglioni "Integration of Molecular Docking and In Vitro Studies: A Powerful Approach for Drug Discovery in Breast Cancer" Appl. Sci. 10, 6981, 2020.
German Advisory Committee Blood (Arbeitskreis Blut), Subgroup Assessment of Pathogens Transmissible by Blood. Human Immunodeficiency Virus (HIV) (Year 2016).
Kaithwas, Gaurav et al. "Linum usitatissimum (linseed/flaxseed) fixed oil: antimicrobial activity and efficacy in bovine mastitis", Inflammopharmacol 19:45-52 (2011). (Year: 2010).
Kwon, Young Do et al. "Crystal Structures of HIV-1 gp120 Envelope Glycoprotein in Complex with NBD Analogues That Target the CD4-Binding Site." PloS one, 9(1): 1-12, (Year: 2014).
Landovitz, Raphael J. et al. "Prevention, treatment and cure of HIV infection" Nature Reviews Microbiology 21(10):657-670, (Year: 2023).
Laskowski, Roman A. & Swindells, Mark B. "LigPlot+: Multiple Ligand-Protein Interaction Diagrams for Drug Discovery." J. Chem. Inf. Model. 51(10): 2778-2786, Sep. 15, 2011.
Mensah, M. B. et al. "Castor oil: a suitable green source of capping agent for nanoparticle syntheses and facile surface functionalization." Royal Society Open Science 5(8):1-19, (Year: 2018).
Miao, Shida et al. "Vegetable-oil-based polymers as future polymeric biomaterials." Acta biomaterialia 10(4):1692-1704 (Year: 2014).
Prévost, Jérémie et al. "The HIV-1 Env gp120 Inner Domain Shapes the Phe43 Cavity and the CD4 Binding Site." MBio 11(3):1-26, May 26, 2020.

(Continued)

*Primary Examiner* — James H Alstrum-Acevedo
*Assistant Examiner* — Justin Christopher Sanchez
(74) *Attorney, Agent, or Firm* — SALIWANCHIK, LLOYD & EISENSCHENK

(57) ABSTRACT

The present invention is directed to a method of treatment or prevention of viral and/or bacterial infection comprising the administration of a polyol derived from a vegetable oil or its derivative. The vegetable oil is preferably linseed oil. The invention is also directed to a formulation comprising a vegetable oil-derived polyol.

13 Claims, 6 Drawing Sheets

(56) References Cited

OTHER PUBLICATIONS

Sharmin, Eram et al. "Studies on microwave synthesized polyol linseed oil." Materials Research Laboratory, Department of Chemistry, pp. 43-45 (Year: 2010).
Sharmin, Eram et al. "Synthesis, characterization, antibacterial and corrosion protective properties of epoxies, epoxy-polyols and epoxy-polyurethane coatings from linseed and Pongamia glabra seed oils." International Journal of Biological Macromolecules 40(5): 407-422 (Year: 2007).
Sierra-Martin, B., & Fernandez-Barbero, A. "Multifunctional hybrid nanogels for theranostic applications." Soft Matter 11(42): 8205-8216, (Year: 2015).
Soni, Kruti S. et al. "Nanogels: an overview of properties, biomedical applications and obstacles to clinical translation." Journal of Controlled Release 240:109-126, Oct. 28, 2016.
Trott, Oleg & Olson, Arthur J. "AutoDock Vina: improving the speed and accuracy of docking with a new scoring function, efficient optimization and multithreading."J. Comput Chem. 31(2):455-461, Jan. 30, 2010.
Vashist, Arti et al. "Interpenetrating biopolymer network based hydrogels for an effective drug delivery system." Carbohydrate Polymers 87(2):1433-1439, Jan. 15, 2012.
Vashist, Arti et al. "Development of Multifunctional Biopolymeric Auto-Fluorescent Micro-and Nanogels as a Platform for Biomedical Applications." Frontiers in Bioengineering and Biotechnology vol. 8, Article 315, pp. 1-16, Apr. 30, 2020.
Woodhouse, Mark et al. "Human viruses: discovery and emergence", Philosophical Transactions of the Royal Society B: Biological Sciences 367:2864-2871, 2012.
Zlatanić, Alisa et al. "Effect of structure on properties of polyols and polyurethanes based on different vegetable oils." Journal of Polymer Science Part B: Polymer Physics 42(5):809-819, Jan. 21, 2004.

* cited by examiner

TREATMENT AND PREVENTION OF INFECTIONS USING VEGETABLE OIL-DERIVED POLYOLS

CROSS-REFERENCE TO A RELATED APPLICATION

This application is a continuation application of U.S. patent application Ser. No. 18/078,414, filed Dec. 9, 2022, which claims priority to U.S. provisional patent application No. 63/287,658 filed Dec. 9, 2021, the entire contents of each of which are incorporated herein by reference in their entirety, including all figures, tables, or drawings.

GOVERNMENT SUPPORT

This invention was made with government support under DA042706 awarded by the National Institutes of Health. The government has certain rights in the invention.

BACKGROUND OF INVENTION

Recent advances in the production of bio-based compounds, natural polymers and other biomaterials using green and natural resources have attracted great attention. In this regard, vegetable oils have shown promising potential and application in the developing field of bio-based compounds. Biomaterials that are synthesized from vegetable oils possess valuable and unique properties such as the inherent biodegradability, high stability, and low cost of raw materials and production of the final biomaterial. A major component of the vegetable oil-derived material is triglycerides, comprising three long fatty acid chains of varying compositions depending on the vegetable oil source. Generally, the length of the chain ranges between C12 and C20, with oleic acid (C18:1), linoleic acid (C18:2) and linolenic acid (C18:3) being the most common. The properties of the biomaterial depend largely on the composition of the fatty acids in the vegetable oil source and the numbers and locations of the double bonds in the fatty acid chain.

Vegetable oil-derived polyols have been reported to be useful as tensioactive agents or organogelators, corrosion inhibitors, and monomers for the synthesis of various macromolecular compounds such as polyurethanes. Natural oils including castor, soybean, camelina, palm kernel, jatropha, and rapeseed oils have been used to synthesize polyols.

While various properties and uses have been reported for vegetable oils, no specific polyols alone are believed to have been used as broad-spectrum antiviral agents. For example, U.S. Pat. No. 10,344,100 and WO2020/247730 disclose hydrogel nanoparticles and microparticles that comprise polyols derived from linseed oil as stabilizers, but they do not teach or suggest using such polyols themselves as therapeutic agents against viral infections.

BRIEF SUMMARY

The present invention provides compositions, methods of treatment, and methods of prevention for viral and/or bacterial infections, where the methods involve administration of a vegetable oil-derived polyol and derivative thereof. Preferably, the vegetable oil is linseed oil. Another aspect of the invention relates to the use of a vegetable oil-derived polyol and derivatives thereof for modifying other compounds such as therapeutic agents. The vegetable oil-derived polyol is preferably linseed oil-derived polyol or derivative thereof. The linseed oil-derived polyol is considered to comprise the chemical structure (I):

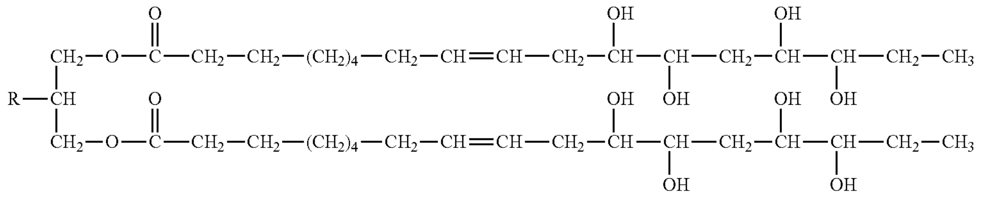

(I)

with R being:

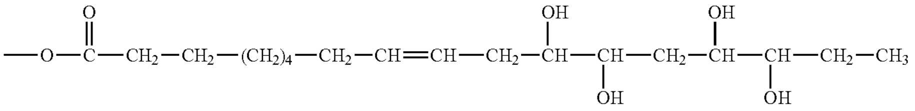

In one aspect, the present invention relates to a method of treating a viral and/or bacterial infection comprising administering to a subject in need of such treatment a vegetable oil-derived polyol or derivative thereof. The vegetable oil-derived polyol or derivative thereof can be formulated into a pharmaceutical composition. Such formulation can optionally include a second therapeutic agent such as a second antiviral agent. The vegetable oil-derived polyol or derivative thereof can be complexed, aggregated, bonded, or otherwise associated with the second therapeutic agent. In preferred embodiments, the vegetable oil is linseed oil.

Another aspect of the present invention relates to a method of preventing a viral and/or bacterial infection comprising administering to a subject in need of such prevention a vegetable oil-derived polyol or derivative thereof. The vegetable oil-derived polyol or derivative thereof can be formulated into a pharmaceutical composition. Such formulation can optionally include a second therapeutic agent such as a second antiviral agent. The vegetable oil-derived polyol or derivative thereof can be complexed, aggregated, bonded, or otherwise associated with the second therapeutic agent. In preferred embodiments, the vegetable oil is linseed oil.

In specific embodiments, the present invention provides a method of treating or preventing an HIV infection in a subject comprising administering to the subject a vegetable oil-derived polyol or derivative thereof. In preferred embodiments, the vegetable oil is linseed oil.

In additional specific embodiments, the present invention provides a method of treating or preventing an infection in a subject by a coronavirus such as SARS-COV-1 and SARS-COV-2, comprising administering to the subject a vegetable oil-derived polyol or derivative thereof. In preferred embodiments, the vegetable oil is linseed oil.

In other specific embodiments, the present invention provides a method of treating or preventing an infection by *Agrobacterium, Streptomyces, Pseudomonas* and/or *Staphylococcus* species in a subject comprising administering to the subject a vegetable oil-derived polyol or derivative thereof. In preferred embodiments, the vegetable oil is linseed oil.

DETAILED DISCLOSURE

Figure 1:
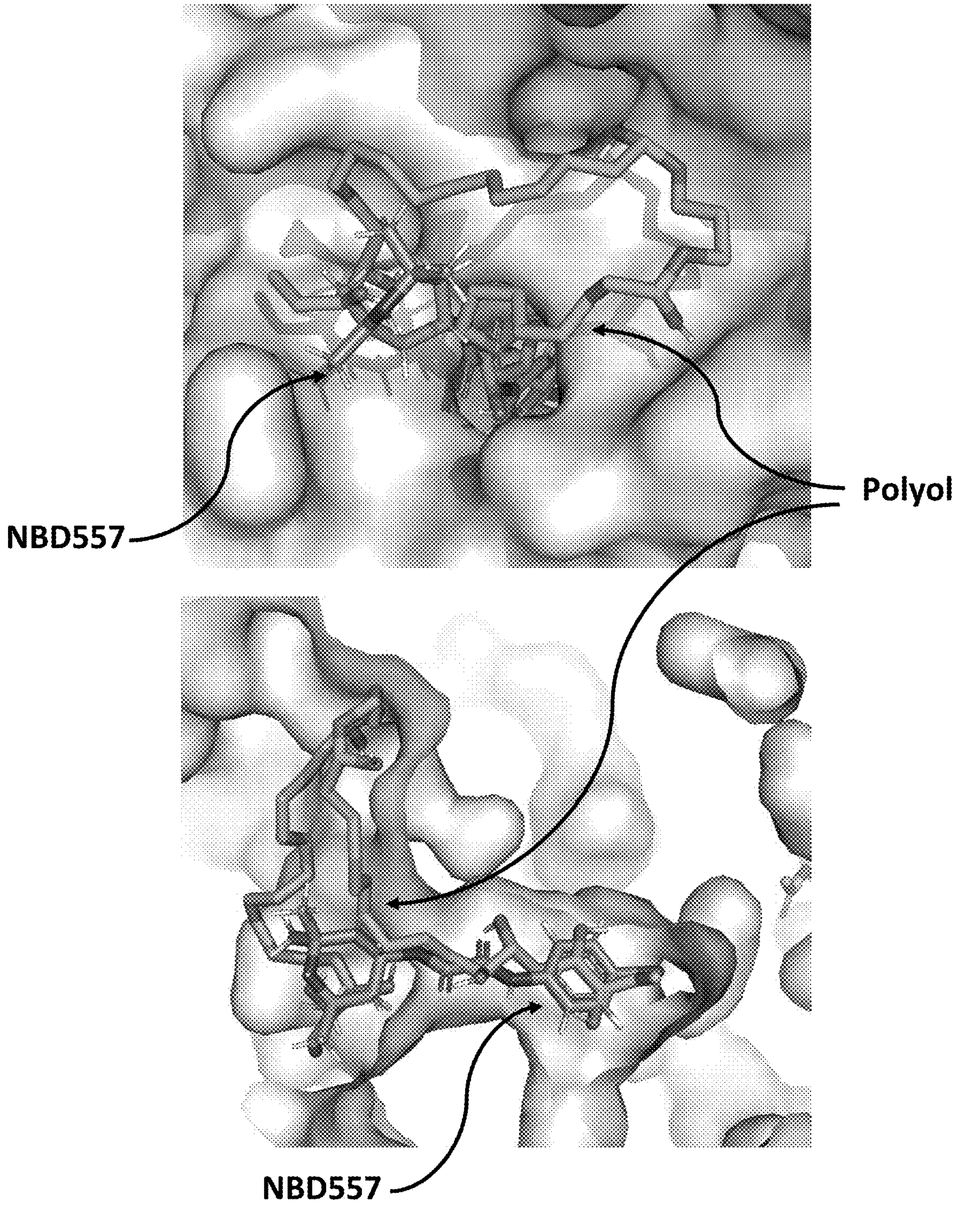
FIG. 1 provides images from a docking study of the linseed oil-derived polyol binding to the CD4 binding site (Phe43 binding cavity) of the HIV envelope glycoprotein gp120 (PDB ID: 4DVR). The structure of the linseed oil-derived polyol is superimposed on the structure of NBD557, also bound to the same site.

The present invention provides antiviral and/or antibacterial formulations comprising a vegetable oil-derived polyol or derivative thereof, methods of treating or preventing viral and/or bacterial infections, the methods involving administration of an effective amount of a vegetable oil-derived polyol or derivative thereof.

The polyols or derivative thereof according to the present invention are derived from vegetable oils by different techniques. A "vegetable oil" as used herein is a natural, plant-based oil including, but are not limited to, castor oil, soybean oil, camelina oil, palm kernel oil, palm oil, jatropha oil, rapeseed oil, sunflower oil, linseed oil, olive oil, black seed oil, and almond oil. Major components of vegetable oils are triglycerides. Fatty acid compositions of the vegetable oil, including the degree of unsaturation, vary depending on the vegetable oil source. Preferably, the polyols according to the present invention is derived from linseed oil.

Polyols derived from vegetable oils as used herein generally have long fatty acid hydrocarbon chains, typically of about C12 to about C20, that have been chemically modified to have one or more hydroxyl groups. The polyols range in the degrees of unsaturation, e.g., C—C double bond.

Various methods known in the art may be used to obtain polyols from vegetable oils according to the present invention. Such methods include, but are not limited to, Baeyer oxidation of the double bonds of polyunsaturated fatty acids or alcoholysis of castor oil with glycerol. Other strategy includes, but are not limited to, ring opening of reactive epoxidized oils with various nucleophilic agents, such as MeOH, phenol, cyclohexanol, diethyl phosphate, phthalic anhydride, diethylene glycol, or lactic acid. Other methods include, but are not limited 10 to, thiol-ene coupling, ozonolysis, hydroformylation, and photochemical oxidation, which are generally described in Miao S. et al., Vegetable-oil-based polymers as future polymeric biomaterials, Acta Biomaterialia 10, 1692-1704, 1693-1694 (2004). In other embodiments, the polyols according to the present invention are synthesized through microwave irradiation in the absence of an organic solvent as disclosed in Sharmin, E. et al., Studies on Microwave 15 Synthesized Polyol Linseed Oil, BVAAP, 18(1), p. 43-45 (2010).

Preferably, the vegetable oil is linseed oil, which is also known as flaxseed oil or flax oil, and can be obtained from the dried, ripened seeds of the flax plant (*Linum usitatissimum*). The preferred polyol is obtained from linseed oil via epoxidation and hydroxylation such as the process described in Sharmin, E. et al., Synthesis, characterization, antibacterial and corrosion protective properties of epoxies, epoxy-polyols and epoxy-polyurethane coatings from linseed and *Pongamia glabra* seed oils, International Journal of Biological Macromolecules, 40 (5): p. 407-422, 408-410 (2007), which is incorporated herein by reference in its entirety. Briefly, the reaction involves mixing of linseed oil and glacial acetic acid with hydrogen peroxide, wherein the ratio of double bonds:acetic acid:hydrogen peroxide is kept at 1:0.5:1.5. The reaction mixture is then heated under constant stirring and regular monitoring, and the final product is washed with sodium bicarbonate aqueous solution, dried, then removed of ether.

The linseed oil-derived polyol is considered to comprise the chemical structure (I):

(I)

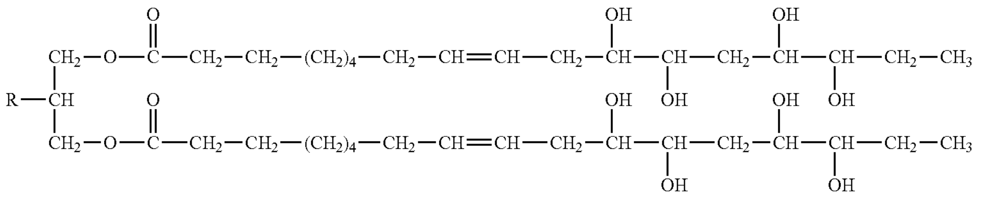

R being:

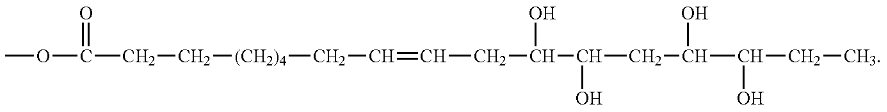

Figure 4:
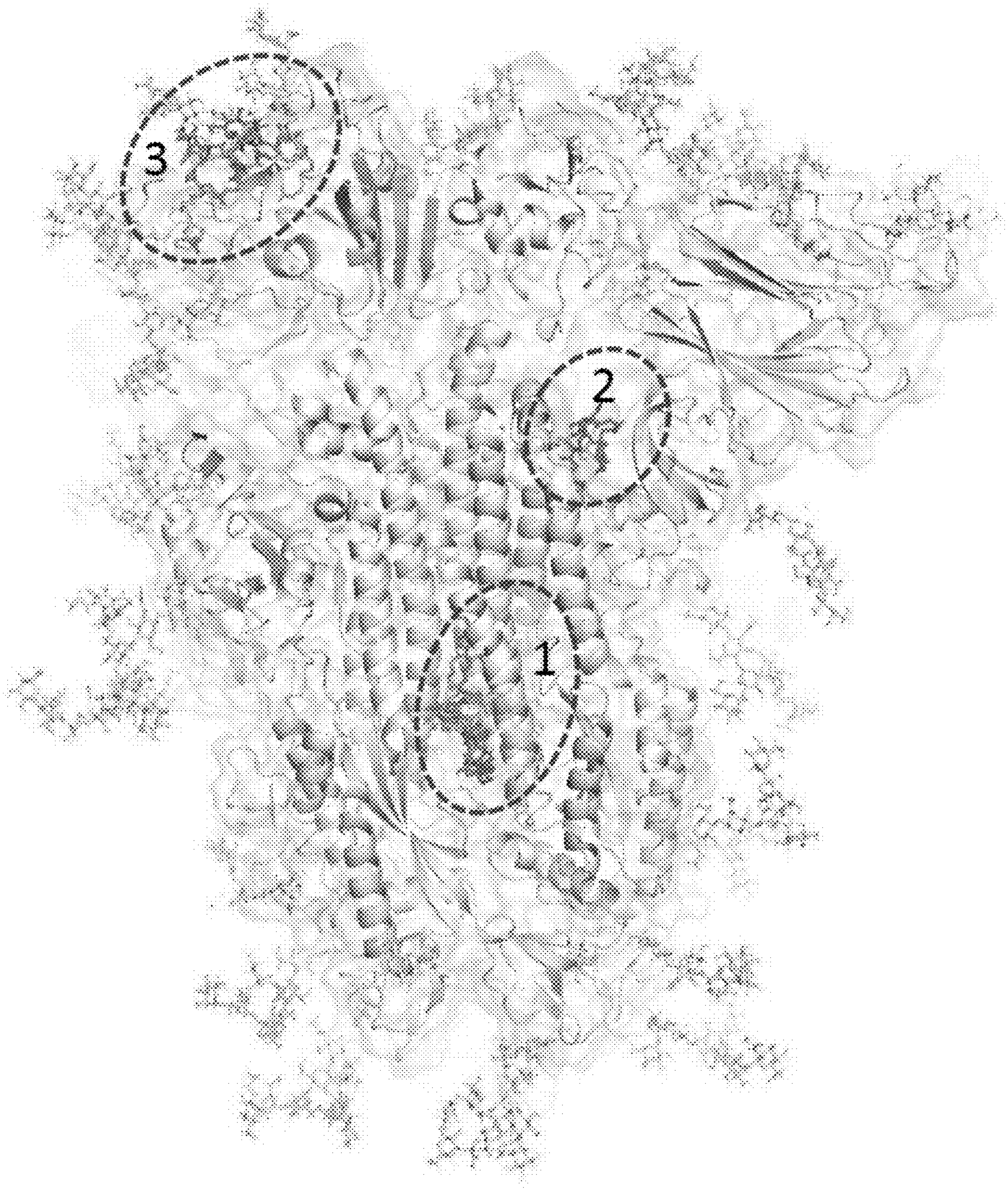
FIG. 4 provides an image from a blind docking study of the linseed oil-derived polyol binding with the fully glycosylated SARS-COV-2 spike protein trimer structure (PDB ID: 6VXX). The image shows the polyol binding at three sites: 1) the top site being the cavity in the fusion core; 2) under the S1 subunit; and 3) near the receptor-binding domain.

It has been surprisingly discovered that polyols derived from vegetable oils such as the linseed oil-derived polyol act as inhibitory compounds against viral infections. For example, in a docking study using the linseed oil-derived polyol of structure (I), the linseed oil-derived polyol was observed to bind to the CD4 binding site of the HIV envelope glycoprotein gp120 (Phe43 binding cavity) (FIG. 1). In a blind docking study performed on the fully glycosylated SARS-CoV-2 Spike protein trimer structure, the linseed oil-derived polyol exhibited binding to three primary sites: 1) the cavity in the fusion core; 2) under the S1 subunit; and 3) near the receptor-binding domain (FIG. 4).

Figure 6:
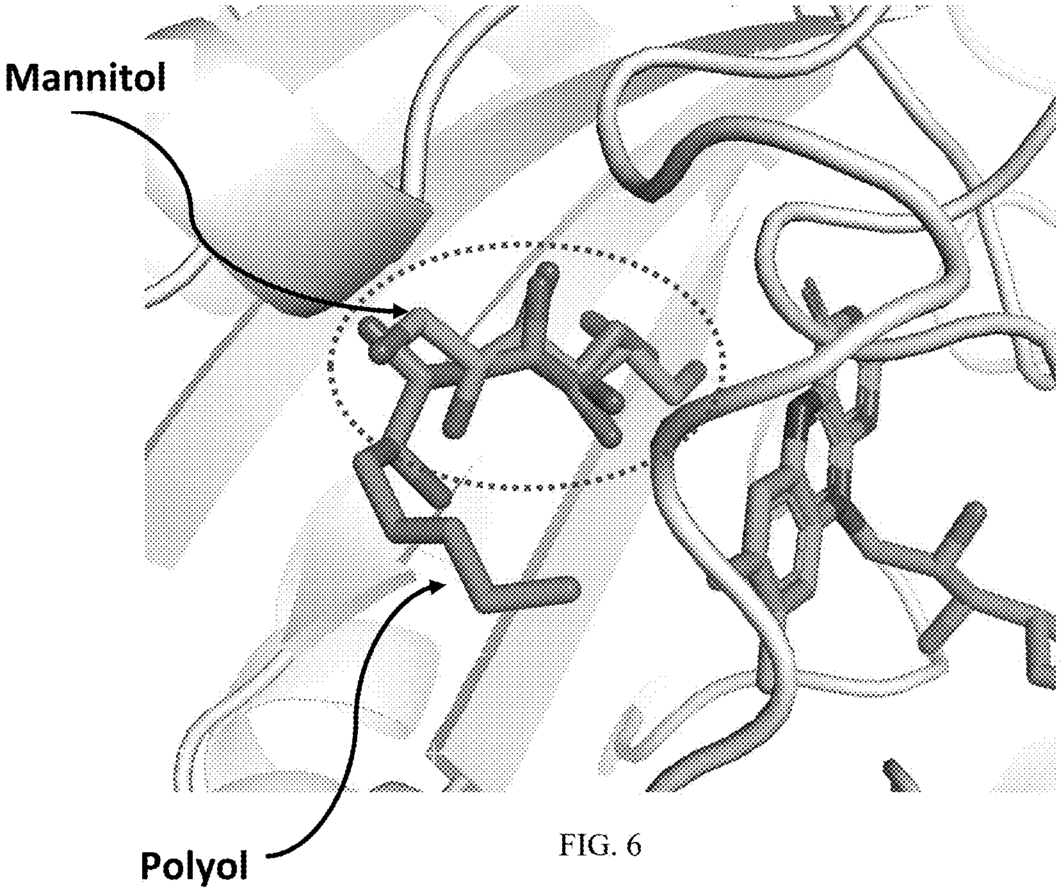
FIG. 6 provides an image from a docking study of a polyol tail of the linseed oil-derived polyol binding to alditol oxidase from *Streptomyces coelicolor* complexed with mannitol (PDB ID: 2VFU).

It has also been discovered that polyols derived from vegetable oils such as the linseed oil-derived polyol have certain antibacterial effect. In a docking study, a polyol tail of the linseed oil-derived polyol was observed to bind to alditol oxidase from *Streptomyces coelicolor* complexed with mannitol (FIG. 6). This suggests that polyols are capable of interfering with sugar alcohol metabolism, including those of *Agrobacterium, Streptomyces, Pseudomonas* and *Staphylococcus* species.

Because the vegetable oil-derived polyols and derivatives thereof bind well to viral and bacterial targets, it can further introduce high efficacy, cellular uptake and/or inhibitory effect of other compounds against viral and/or bacterial infections. The vegetable oil-derived polyols and derivatives thereof according to the present invention can have one or more target sites in a single protein or bioactive.

Figure 2:
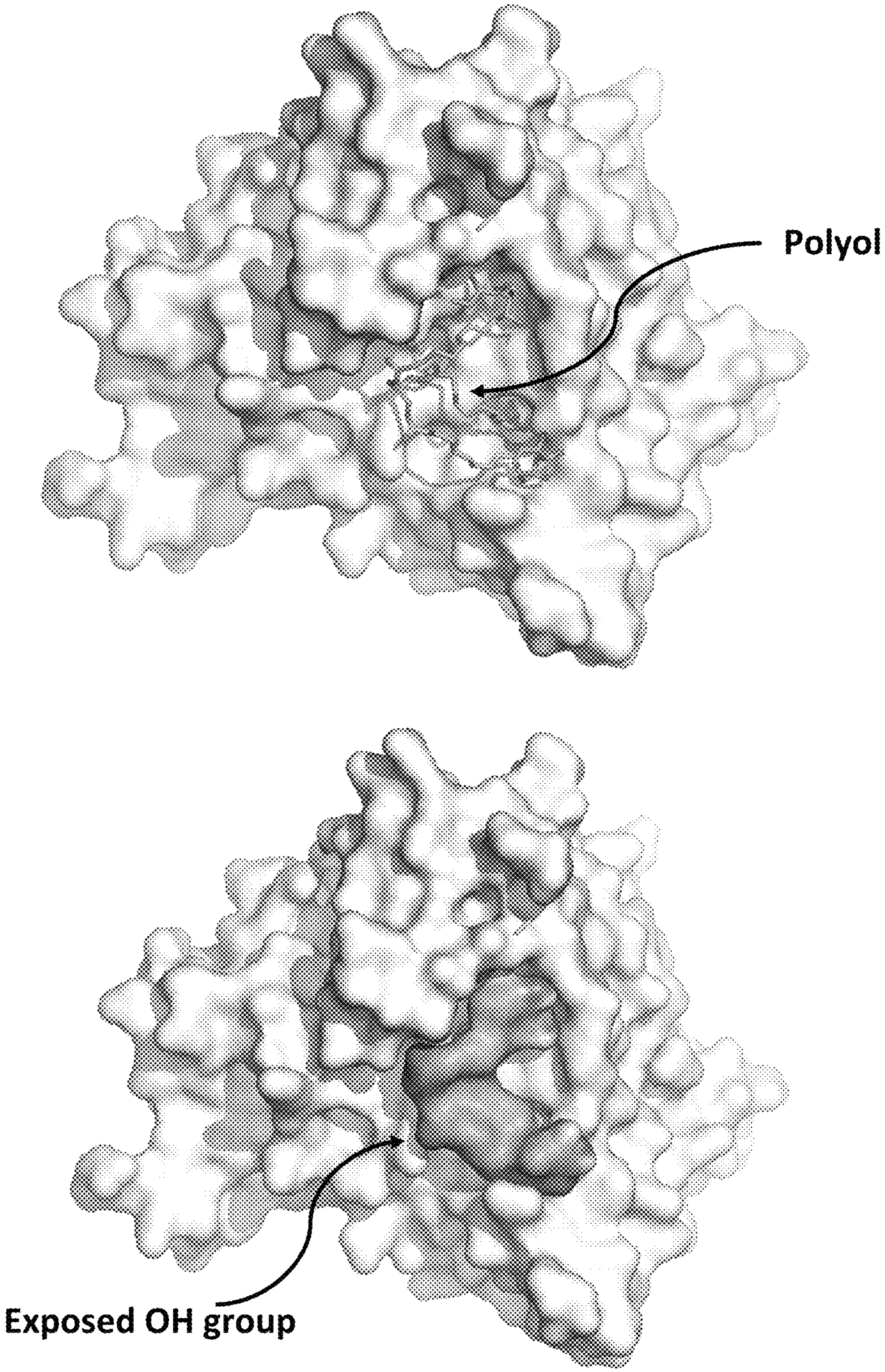
FIG. 2 provides images from a docking study of the linseed oil-derived polyol binding to the CD4 binding site of gp120 (Phe43 binding cavity). The images show that one of the three fatty acid chains of the polyol inserts into the binding cavity while the other two do not, exposing the free hydroxyl (—OH) groups.

As an example of functional capacities of the vegetable oil-derived polyol, the docking study with HIV envelope glycoprotein gp120 revealed that one of the three fatty acid chains of the linseed oil-derived polyol inserts into the CD4-binding cavity, while the other two do not, leaving their free hydroxyl (OH) groups exposed (FIG. 2). Advantageously, these exposed OH groups are available as reactive sites for complexing, aggregating, bonding or otherwise associating with other compounds. Exemplary modifications to one or more of the free hydroxyl groups of the vegetable oil-derived polyol include, but are not limited to, functionalization with a substituted or unsubstituted phenyl or heteroaryl ring, the substituted phenyl or heteroaryl ring having one or more substituent independently chosen from a halogen atom. In some embodiments, the substituted phenyl ring is meta-fluoro phenyl.

In additional embodiments, the vegetable oil-derived polyols are modified with chitosan, other cellulose, or their derivative such as hydroxy propyl, hydroxy butyl, alkylated, or halogenated derivative. In other embodiments, halogenated or phenylated glutaraldehyde is used as a crosslinker to modify polyol-based nano-formulations.

In some embodiments, it is further contemplated that the vegetable oil-derived polyols are provided in a polymerized form via direct polymerization of epoxidized vegetable oils. Transesterification can also be utilized to modify the vegetable oil-derived polyols generally.

In some embodiments, the vegetable oil-derived polyol or derivative thereof is complexed, aggregated, bonded, or otherwise associated with other compounds such as other therapeutic agents including antiviral agents, antibacterial agents, and/or polymers. The therapeutic agent with which the vegetable oil-derived polyol or derivative thereof is complexed, aggregated, bonded or otherwise associated may be hydrophilic or hydrophobic. In certain embodiments, the vegetable oil-derived polyol or derivative thereof can be used to modify other compounds to increase their hydrophobicity while targeting the surface protein of a virus. As further non-limiting examples, the vegetable oil-derived polyol or derivative thereof can be used to modify various polymers such as polyurethanes, Poly(vinyl alcohol) (PVA), Polyvinyl chloride (PVC), Polyvinylpyrrolidone (PVP). Other polymers include but are not limited to biopolymers, guar gum, poly(lactic-co-glycolic acid) (PLGA), chitin, polylactic acid (PLA), Hyaluronic acid, Polyacrylamide, as well as synthetic polymers. The vegetable oil-derived polyol or derivative thereof can also be used to modify various coatings and resins, waterborne polymers, nanocomposite materials which include dendrimers, liposomes, etc. Furthermore, the vegetable oil-derived polyol or derivative thereof can be used to modify nanocapsules, magnetic particles as well as the carbon nanotubes for functionalization.

In some embodiments, it is further contemplated that the vegetable oil-derived polyol can be incorporated into polyglycerol-based dendrons and megamers, such as those disclosed in Miao S. et al., Vegetable-oil-based polymers as future polymeric biomaterials, Acta Biomaterialia 10, 1692-1704, 1699-1700 (2004), incorporated herein in its entirety.

Preferably, such complexation, aggregation, bonding, or association does not interfere with the antiviral or antibacterial effect of the vegetable oil-derived polyol. More preferably, such complexation, aggregation, bonding, or association has a synergistic effect on at least one property. In specific embodiments, the vegetable oil-derived polyol or derivative thereof is not part of a hydrogel nanoparticle or microparticle.

In some embodiments, the vegetable oil-derived polyol or derivative thereof can be formulated into a pharmaceutically acceptable composition. In other embodiments, the vegetable oil-derived polyol or derivative thereof alone serves as an antiviral or antibacterial agent. In yet other embodiments, the vegetable oil-derived polyol or derivative thereof is not complexed, aggregated, bonded or otherwise associated with a polymeric compound or any therapeutic agent. In specific embodiments, the vegetable oil-derived polyol or derivative thereof is not part of a hydrogel nanoparticle or microparticle.

The various embodiments of the present invention have one or more of the following advantageous features: (a) sustainability of production, as the source of polyols used in the present invention can be vegetable oil, which is one of the most important classes of biological resources; (b) broad applicability to treat infections by a wide range of viruses including SARS-CoV-2 and HIV; (c) low cost of raw materials; (d) inherent biodegradability of the polyols; (e) safe production methodologies; and (f) suitability of modifications and linking to other compounds such as therapeutic agents and/or polymers for stabilization and synergy.

The formulation according to the present invention comprising the vegetable oil-derived polyol or derivative thereof may further comprise a pharmaceutically acceptable carrier or excipient. "Pharmaceutically acceptable carrier" or "pharmaceutically acceptable excipient" includes, without limitation, any solvents, aqueous vehicles, water-miscible vehicles, non-aqueous vehicles, adjuvants, solubility enhancers, glidants, diluents, isotonic agents, surfactants, wetting agents, suspending and dispersing agents, stabilizers, isotonic agents, wetting agents, emulsifiers, sequestering or chelating agents, coatings, absorption delaying agents, cryoprotectants, lyoprotectants, thickening agents, preservatives, pH adjusting agents, sweetening agents, dye or colorants, flavoring agents or enhancers, and the like. Carriers and excipients suitable for use in formulations and such embodiments are within the purview of the invention. A pharmaceutically acceptable carrier or excipient preferably is approved or approvable by a regulatory agency of the Federal or State government, listed in the U.S. Pharmacopoeia, or other generally recognized pharmacopoeia for use in animals and more particularly in humans. Except insofar as any such carriers or excipients are incompatible with the vegetable oil-derived polyol or derivative thereof, their use in the formulation of the invention is contemplated.

Depending on the type of formulation and/or mode of administration thereof, pharmaceutically acceptable carriers and excipients include, but are not limited to, water or Water for Injection USP, Sodium Chloride Injection, Ringer's Injection, Dextrose Injection, Dextrose, Sodium Chloride Injection, Lactated Ringer's Injection. Further examples of the carriers and excipients include, but are not limited to, ethanol, glycerol, propylene glycol, polyethylene glycol, and polypropylene glycol, vegetable oils, liquid sucrose, sorbitol, isopropyl myristate, and benzyl benzoate. Examples of preservatives can include, but are not limited to, antibacterial and antifungal agents, for example, parabens, benzoates, chlorobutanol, phenol, ascorbic acid, thimerosal, and the like. Examples of isotonic agents include, but are not limited to, sugars, sodium chloride, mannitol, and sorbitol. Prolonged absorption of injectable compositions can be achieved by including in the composition an agent which delays absorption, for example, aluminum monostearate or gelatin. Suspending agents may be methyl cellulose, sodium carboxymethyl cellulose, tragacanth, or sodium alginate. Examples of typical wetting agents include, but are not limited to, lecithin and polysorbate 80. Where necessary, the formulation may also include a local anesthetic such as lidocaine if administration of the formulation causes pain at the site of administration.

Typically, the vegetable oil-derived polyols and derivatives thereof according to the present invention are formulated into pharmaceutical compositions using techniques and procedures known in the art. In some embodiments, the vegetable oil-derived polyols and derivatives thereof are formulated into aerosols, inhalants, tablets, capsules, or elixirs for oral administration or in sterile solutions or suspensions for parenteral administration. In other embodiments, the formulation comprising vegetable oil-derived polyols and derivatives thereof, together with an adjuvant or a pharmaceutically acceptable carrier, may be placed into the form of solids including pills, troches, tablets, cachets, lozenges, filled capsules, powder and pellet forms, and liquids such as aqueous or non-aqueous solutions, suspensions, emulsions, elixirs, and capsules filled with the same. The formulation may further comprise conventional ingredients in conventional proportions, with or without additional therapeutic agents.

The tablets, troches, pastilles, pills, capsules, and the like may also contain one or more of the following: binders such as gum tragacanth, acacia, corn starch or gelatin; excipients such as dicalcium phosphate; a disintegrating agent such as corn starch, potato starch, alginic acid, and the like; a lubricant such as magnesium stearate; and a sweetening agent such as sucrose, fructose, lactose, or aspartame, or a flavoring agent such as peppermint, oil of wintergreen, or cherry flavoring may be added. Various other materials may be present as coatings or for otherwise modifying the physical form of the solid unit dosage form. For instance, tablets, pills, or capsules may be coated with gelatin, wax, shellac, or sugar, and the like.

In other embodiments, the formulation according to the present invention may be a liquid solution, for example a single-phase solution, a suspension, an aqueous or non-aqueous liquid, or an oil-in-water or water-in-oil liquid emulsion. The formulation may also be in the form of syrup or mouth washes and the like. The vegetable oil-derived polyol or derivative thereof of the present invention may also be administered as a bolus, electuary, paste, or incorporated directly into the subject's diet.

Formulations suitable for injectable use may include sterile aqueous solutions, dispersions, and sterile powders for the extemporaneous preparation of sterile injectable solutions or dispersions. In all cases, the formulation should be sterile and must be sufficiently fluid before administration to facilitate syringeability. The formulation should be stable under the conditions of manufacture and storage, and should be preserved against contamination by microorganisms. Sterile injectable solutions can be prepared by incorporating the vegetable oil-derived polyol or its derivative in the required amount in an appropriate solvent with one or a combination of ingredients enumerated above, as required, followed by filtered sterilization. Generally, dispersions are prepared by incorporating a therapeutic agent into a sterile vehicle which contains a basic dispersion medium and other required ingredients from those enumerated above. In the case of sterile powders for the preparation of sterile injectable solutions, methods of preparation include vacuum drying and freeze-drying which yields a powder of the active ingredient (i.e., the vegetable oil-derived polyol or its derivative) plus any additional desired ingredient from a previously sterile-filtered solution thereof.

The formulations according to the present invention may be suitable for topical administration and can be formulated as ointments, creams, lotions, gels, or as a transdermal patch. Transdermal patches can contain penetration enhancers such as linalool, carvacrol, thymol, citral, menthol, t-anethole, and the like. Ointments and creams can, for example, include an aqueous or oily base with the addition of suitable thickening agents, gelling agents, colorants, and the like. Lotions and creams can include an aqueous or oily base and typically also contain one or more emulsifying agents, stabilizing agents, dispersing agents, suspending agents, thickening agents, coloring agents, and the like. Gels preferably include an aqueous carrier base and include a gelling agent such as cross-linked polyacrylic acid polymer, a derivatized polysaccharide (e.g., carboxymethyl cellulose), and the like.

Formulations suitable for intra-nasal administration are also encompassed by the present invention. Such intra-nasal compositions comprise the vegetable oil-derived polyol or derivative thereof, in a vehicle and suitable administration device to deliver a liquid spray, dispersible powder, or drops. Drops may be formulated, for example as a suspension, with an aqueous or non-aqueous base also comprising one or more dispersing agents, solubilizing agents, or suspending agents. Liquid sprays can be conveniently delivered from a pressurized pack, an insufflator, a nebulizer, or other means of delivering an aerosol. A pharmaceutical formulation suitable for administration as an aerosol may be in the form of a liquid comprising an aqueous carrier. A surfactant may be present which lowers the surface tension of the formulation sufficiently to result in the formation of droplets within the desired size range when subjected to nebulization.

The vegetable oil-derived polyol or derivative thereof may be inhaled or insufflated as part of a dry powder composition comprising an inert powdered carrier such as lactose or starch. Such powder composition can be provided in unit dosage form, for example, in capsules, cartridges, gelatin packs, or blister packs, from which the powder can be administered with the aid of an inhalator or insufflator.

Because the formulation according to the present invention possesses antiviral and antibacterial properties, it can be used to treat a viral or bacterial infection in a subject. Furthermore, the formulation can also be used prophylactically, such that it can be used particularly prior to a subject's potential exposure to a virus. For example, the formulation according to the present invention can be applied to bodily surfaces such as genitals that are likely to be the point of viral entry. As another example, the formulation in the form of pills or capsules can be ingested in a prophylactic capacity prior to the subject's contact with a person who is potentially infected with a virus.

In a further aspect, the present invention is directed to a method for treating a subject infected with a virus or bacteria. The method comprises administering to a subject a formulation comprising a vegetable oil-derived polyol or its derivative.

In another aspect, the present invention is also directed to a method of preventing viral infection or viral replication in a subject. The method comprises administering to a subject a vegetable oil-derived polyol or its derivative.

In further aspects, the present invention provides a method for preventing and/or treating a viral infection in a host cell. The method comprises administering to the host cell a vegetable oil-derived polyol or its derivative.

In other aspects, the present invention provides a method for inhibiting viral replication in a host cell, prior to and/or after the infection of the host cell by a virus, e.g., HIV or SARS-COV-2. The method comprises administering to the host cell a vegetable oil-derived polyol or its derivative.

Other aspects of the present invention provide a method for modulating the immune response of a host cell, comprising administering to the host cell a vegetable oil-derived polyol or its derivative.

In specific embodiments, the vegetable oil-derived polyol or its derivative is administered to the host cell in an effective amount at a concentration ranging, for example, from 0.1 μg/ml to 500 μg/ml, from 1 μg/ml to 450 μg/ml, from 1 μg/ml to 400 μg/ml, from 5 μg/ml to 400 μg/ml, from 10 μg/ml to 350 μg/ml, from 10 μg/ml to 300 μg/ml, from 25 μg/ml to 250 μg/ml, from 50 μg/ml to 200 μg/ml, from 50 μg/ml to 150 μg/ml, from 75 μg/ml to 200 μg/ml, or from 100 μg/ml to 200 μg/ml.

"Subject" refers to an animal, such as a mammal, for example a human. The methods described herein can be useful in both human therapeutics and veterinary applications. In some embodiments, the subject is a mammal (including animal models of disease), and in some embodiments, the subject is human. Non-limiting examples of subjects include canine, porcine, rodent, feline, bovine, poultry, equine, human, and non-human primates.

The term "treatment" or any grammatical variation thereof (e.g., treat, treating, etc.), as used herein, includes but is not limited to, the application or administration to a subject (or application or administration to a cell or tissue from a subject) with the purpose of delaying, slowing, stabilizing, curing, healing, alleviating, relieving, altering, remedying, less worsening, ameliorating, improving, or affecting the disease or condition, or the symptom of the disease or condition. The term "treating" refers to any indication of success in the treatment or amelioration of a pathology or condition, including any objective or subjective parameter such as abatement; remission; lessening of the rate of worsening; lessening severity of the disease; stabilization, diminishing of symptoms or making the pathology or condition more tolerable to the subject; or improving a subject's physical or mental well-being.

The phrases "pharmacologically effective amount" and "therapeutically effective amount" or simply "effective amount" refer to that amount of an active ingredient(s) sufficient to produce the intended pharmacological, therapeutic, or preventive result. For example, if a given clinical treatment is considered effective when there is at least a 20% reduction in a measurable parameter associated with a disease or disorder, a therapeutically effective amount of the active ingredient(s) for the treatment of that disease or disorder is the amount necessary to affect at least a 20% reduction in that parameter.

The term "prevention" or any grammatical variation thereof (e.g., prevent, preventing, etc.), as used herein, includes but is not limited to, at least the reduction of likelihood of the risk of (or susceptibility to) acquiring a disease or disorder (i.e., causing at least one of the clinical symptoms of the disease not to develop in a patient that may be exposed to or predisposed to the disease but does not yet experience or display symptoms of the disease). The term "prevention" may refer to avoiding, delaying, forestalling, or minimizing one or more unwanted features associated with a disease or disorder, and/or completely or almost completely preventing the development of a disease or disorder and its symptoms altogether. Prevention can further include, but does not require, absolute or complete prevention, meaning the disease or disorder may still develop at a later time and/or with a lesser severity than it would without preventative measures. Prevention can include reducing the severity of the onset of a disease or disorder, and/or inhibiting the progression thereof.

The vegetable oil-derived polyol or derivative thereof according to the present invention can be administered to a subject by any appropriate mode including, but are not limited to, oral, rectal, bronchial, nasal, topical, buccal, sub-lingual, transdermal, vaginal, intramuscular, intraperitoneal, intravenous, intra-arterial, subcutaneous, intracerebral, intraocular administration or in a form suitable for administration by inhalation or insufflation, including powders and liquid aerosol administration, or intraparenteral infusion. Administration may be also by way of other carriers or vehicles such as patches, micelles, liposomes, vesicles, implants (e.g., microimplants), synthetic polymers, and the like. In some embodiments, the mode of administration is oral. In other embodiments, the mode of administration is subcutaneous, intravenous, or intraperitoneal. In yet other embodiments, the mode of administration is nasal.

The particular mode of administration as well as the dosage regimen designed to deliver an effective amount of the vegetable oil-derived polyol or its derivative are appropriately decided, taking into account factors such as age, sex, and particulars of the subject, as well as the virus, the disease, and the disease state involved, and whether the purpose is preventative. Administration of an effective amount of the vegetable oil-derived polyol or derivative thereof may be accomplished in daily or multi-daily doses of the vegetable oil-derived polyol or derivative thereof over a period of a few days to months, or even years. If the vegetable oil-derived polyol or derivative thereof is administered with another therapeutic agent, the effective amount of the vegetable oil-derived polyol or derivative thereof may be in the same range as is typical for use of that agent as a monotherapy, or the amount may be lower than a typical monotherapy amount especially if the combination therapy results in a synergy.

In general, however, a suitable dose of the vegetable oil-derived polyol or derivative thereof will be in the range of from about 0.001 to about 100 mg/kg of body weight per day, preferably from about 0.01 to about 100 mg/kg of body weight per day, more preferably, from about 0.1 to about 50 mg/kg of body weight per day, or even more preferred, in a range of from about 1 to about 10 mg/kg of body weight per day. For example, a suitable dose may be about 1 mg/kg, 10 mg/kg, or 50 mg/kg of body weight per day.

The vegetable oil-derived polyol or derivative thereof can be conveniently administered in unit dosage form, containing for example, about 0.05 to about 10000 mg, about 0.5 to about 10000 mg, about 5 to about 1000 mg, or about 50 to about 500 mg of the vegetable oil-derived polyol or derivative thereof per unit dosage form. In some embodiments, about 1 ml to about 3 ml of the total formulation comprises about 1% to about 2% by weight of the vegetable oil-derived polyol or derivative thereof, which can be administered in a single dose or multiple doses. In other embodiments, the formulation comprises about 0.5% to about 5% by weight of the vegetable oil-derived polyol or derivative thereof, to be administered in a single dose or multiple doses.

The vegetable oil-derived polyol or derivative thereof may be provided in a single dose or as divided doses administered at appropriate intervals, for example, as one dose per day or as two, three, four or more sub-doses per day. The sub-dose itself may be further divided, e.g., into a number of discrete loosely spaced administrations.

The vegetable oil-derived polyol or derivative thereof of the present invention may be formulated into pharmaceutical compositions using techniques and procedures known in the art and as described herein. In other embodiments, the vegetable oil-derived polyol or derivative thereof is administered to a subject by itself or incorporated directly into the subject's diet.

The methods according to the present invention may further comprise administrating one or more other therapeutic agents, i.e., in the form of a combination therapy. The other therapeutic agent(s) can be provided within a therapeutically useful and effective range of amounts in the same or a separate formulation. The amount of any additional therapeutic agent(s) may be in the same range as is typical for use of that agent as a monotherapy, or the amount may be lower than a typical monotherapy amount if the combination therapy results in a synergy.

In specific embodiments, the vegetable oil-derived polyol or derivative thereof is formulated with a therapeutic agent capable of treating diseases caused by a viral infection. The therapeutic agent may also be an antagonist of opiates. The combination of the vegetable oil-derived polyol or derivative thereof and an opiate antagonist may be used as Pre-exposure prophylaxis (PrEP) agents as first line of defense against HIV, in particular, in high-risk groups. Such combined therapy may have universal applicability against viral infections and thus, offers treatment of opiate-associated neuronal abnormalities and AIDS.

Non-limiting examples of other therapeutic agents include, but are not limited to, natural enzymes, proteins derived from natural sources, recombinant proteins, natural peptides, synthetic peptides, cyclic peptides, antibodies, cytotoxic agents, immunoglobins, beta-adrenergic blocking agents, calcium channel blockers, coronary vasodilators, cardiac glycosides, antiarrhythmics, cardiac sympathomimetics, angiotensin converting enzyme (ACE) inhibitors, diuretics, inotropes, cholesterol and triglyceride reducers, bile acid sequestrants, fibrates, 3-hydroxy-3-methylgluteryl (HMG)-CoA reductase inhibitors, niacin derivatives, antiadrenergic agents, alpha-adrenergic blocking agents, centrally acting antiadrenergic agents, vasodilators, potassium-sparing agents, thiazides and related agents, angiotensin II receptor antagonists, peripheral vasodilators, antiandrogens, estrogens, antibiotics, retinoids, insulins and analogs, alpha-glucosidase inhibitors, biguanides, meglitinides, sulfonylureas, thiazolidinediones, androgens, progestogens, bone metabolism regulators, anterior pituitary hormones, hypothalamic hormones, posterior pituitary hormones, gonadotropins, gonadotropin-releasing hormone antagonists, ovulation stimulants, selective estrogen receptor modulators, antithyroid agents, thyroid hormones, bulk forming agents, laxatives, antiperistaltics, flora modifiers, intestinal adsorbents, intestinal anti-infectives, antianorexic, anticachexic, antibulimics, appetite suppressants, antiobesity agents, antacids, upper gastrointestinal tract agents, anticholinergic agents, aminosalicylic acid derivatives, biological response modifiers, corticosteroids, antispasmodics, 5-HT4 partial agonists, antihistamines, cannabinoids, dopamine antagonists, serotonin antagonists, cytoprotectives, histamine H2-receptor antagonists, mucosal protective agent, proton pump inhibitors, *H. pylori* eradication therapy, erythropoieses stimulants, hematopoietic agents, anemia agents, heparins, antifibrinolytics, hemostatics, blood coagulation factors, adenosine diphosphate inhibitors, glycoprotein receptor inhibitors, fibrinogen-platelet binding inhibitors, thromboxane-A2 inhibitors, plasminogen activators, antithrombotic agents, glucocorticoids, mineralcorticoids, corticosteroids, selective immunosuppressive agents, antifungals, drugs involved in prophylactic therapy, AIDS-associated infections, cytomegalovirus, non-nucleoside reverse transcriptase inhibitors, nucleoside analog reverse transcriptase inhibitors, protease inhibitors, anemia, Kaposi's sarcoma, aminoglycosides, carbapenems, cephalosporins, glycopeptides, lincosamides, macrolies, oxazolidinones, penicillins, streptogramins, sulfonamides, trimethoprim and derivatives, tetracyclines, anthelmintics, amebicides, biguanides, cinchona alkaloids, folic acid antagonists, quinoline derivatives, *Pneumocystis carinii* therapy, hydrazides, imidazoles, triazoles, nitroimidazoles, cyclic amines, neuraminidase inhibitors, nucleosides, phosphate binders, cholinesterase inhibitors, adjunctive therapy, barbiturates and derivatives, benzodiazepines, gamma aminobutyric acid derivatives, hydantoin derivatives, iminostilbene derivatives, succinimide derivatives, anticonvulsants, ergot alkaloids, antimigraine preparations, biological response modifiers, carbamic acid eaters, tricyclic derivatives, depolarizing agents, nondepolarizing agents, neuromuscular paralytic agents, CNS stimulants, dopaminergic reagents, monoamine oxidase inhibitors, COMT inhibitors, alkyl sulphonates, ethylenimines, imidazotetrazines, nitrogen mustard analogs, nitrosoureas, platinum-containing compounds, antimetabolites, purine analogs, pyrimidine analogs, urea derivatives, anthracyclines, actinomycins, camptothecin derivatives, epipodophyllotoxins, taxanes, *vinca* alkaloids and analogs, antiandrogens, antiestrogens, nonsteroidal aromatase inhibitors, protein kinase inhibitor antineoplastics, azaspirodecanedione derivatives, anxiolytics, stimulants, monoamine reuptake inhibitors, selective serotonin reuptake inhibitors, antidepressants, benzisooxazole derivatives, butyrophenone derivatives, dibenzodiazepine derivatives, dibenzothiazepine derivatives, diphenylbutylpiperidine derivatives, phenothiazines, thienobenzodiazepine derivatives, thioxanthene derivatives, allergenic extracts, nonsteroidal agents, leukotriene receptor antagonists, xanthines, endothelin receptor antagonist, prostaglandins, lung surfactants, mucolytics, antimitotics, uricosurics, xanthine oxidase inhibitors, phosphodiesterase inhibitors, metheamine salts, nitrofuran derivatives, quinolones, smooth muscle relaxants, parasympathomimetic agents, halogenated hydrocarbons, esters of amino benzoic acid, amides (e.g., lidocaine, articaine hydrochloride, bupivacaine hydrochloride), antipyretics, hynotics and sedatives, cyclopyrrolones, pyrazolopyrimidines, nonsteroidal anti-inflammatory drugs, opioids, para-aminophenol derivatives, alcohol dehydrogenase inhibitor, heparin antagonists, adsorbents, emetics, opioid antagonists, cholinesterase reactivators, nicotine replacement therapy, vitamin A analogs and antagonists, vitamin B analogs and antagonists, vitamin C analogs and antagonists, vitamin D analogs and antagonists, vitamin E analogs and antagonists, and vitamin K analogs and antagonists. Preferred therapeutic agents are those targeting the surface proteins of viruses. Other preferred therapeutic agents include those affecting bacterial dehydrogenase activities.

As described herein, the vegetable oil-derived polyols and their derivatives of the present invention are useful as therapeutic agents against viral infections. In one embodiment, the viral infection may be caused by, for example, RNA viruses including retroviruses (e.g., lentiviruses such as HIV) and coronaviruses (e.g., viruses that cause COVID-19). Example of the viruses include, but are not limited to, Orthomyxoviruses, Adenovirus, Hepatitis C Virus (HCV), Zika, SARS-COV (Severe Acute Respiratory Syndrome-Corona Virus), the coronavirus that causes COVID-19, Dengue, Ebola, Influenza A/B/C virus, polio measles, primate foamy virus, HIV, COV MERS (Middle East Respiratory Syndrome virus), HCoV-NL63, HCoV-OC43, HCoV-229E, HCoV-HKU1, adult T-cell leukemia virus (ATLV), Human T-cell lymphotropic virus type 1 (HTLV-1), and type II (HTLV-2). Preferably, the virus is HIV-1, HIV-2, SARS-COV-1 or SARS-COV-2. Furthermore, mutated and/or truncated viruses derived from the above viruses are encompassed by the present invention.

Other viruses include, for example, avian leukemia virus, avian sarcoma virus, avian reticuloendotheliosis virus, murine mammary cancer virus, murine leukemia virus, murine sarcoma virus, guinea pig type C virus, hamster type C virus, rat leukemia virus, feline leukemia virus, feline sarcoma virus, feline type C virus, ovine leukemia virus, bovine leukemia virus, swine type C virus, simian leukemia virus, Mason-Pfizer virus, simian sarcoma virus, simian T-lymphotropic virus, baboon type C virus, visna virus, EIAV, spuma virus, ovine progressive pneumonia virus, ovine maedi virus, simian T-lymphotropic virus type III (STLV-III), equine infectious anemia virus, Bovine immunodeficiency virus (BIV), the Feline immunodeficiency virus (FIV), the Simian immunodeficiency virus (SIV), feline Coronavirus (FCOV), and Mouse Hepatitis Virus (MHV-LUC).

In specific embodiments, the present invention provides a method for preventing an infection by and/or treating a disease caused by, an RNA virus, e.g., retrovirus or coronavirus. The method comprises administering a vegetable oil-derived polyol or derivative thereof to a subject who is infected with, or susceptible to infection by, an RNA virus.

In some embodiments, the disease may be, for example, Zika, Ebola, Hepatitis C, Influenza, COVID-19, MERS, SARS, AIDS, adult T-cell lymphoma (ATL), Dengue fever, and progressive general lymphadenosis (PGL). Preferably, the disease is AIDS or COVID-19.

In specific embodiments, the present invention provides a method for treating and/or preventing an infection and/or a disease caused by bacteria by administering to the subject an effective amount of a vegetable oil-derived polyol or derivative thereof, said vegetable oil-derived polyol or derivative thereof inhibiting sugar alcohol metabolism by the bacteria. In some embodiments, the bacteria are species of *Agrobacterium, Streptomyces, Pseudomonas* or *Staphylococcus.*

As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising." The transitional terms/phrases (and any grammatical variations thereof) "comprising," "comprises," and "comprise" can be used interchangeably; "consisting essentially of," and "consists essentially of" can be used interchangeably; and "consisting," and "consists" can be used interchangeably.

The transitional term "comprising," "comprises," or "comprise" is inclusive or open-ended and does not exclude additional, unrecited elements or method steps. By contrast, the transitional phrase "consisting of" excludes any element, step, or ingredient not specified in the claim. The phrases "consisting" or "consists essentially of" indicate that the claim encompasses embodiments containing the specified materials or steps and those that do not materially affect the basic and novel characteristic(s) of the claim. Use of the term "comprising" contemplates other embodiments that "consist" or "consisting essentially of" the recited component(s).

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 0-20%, 0 to 10%, 0 to 5%, or up to 1% of a given value. Where particular values are described in the application and claims, unless otherwise stated the term "about" meaning within an acceptable error range for the particular value should be assumed.

When ranges are used herein, such as for dose ranges, combinations and subcombinations of ranges (e.g., subranges within the disclosed range), specific embodiments therein are intended to be explicitly included.

Methods and Materials

Molecular Docking Studies

Molecular docking protocols are widely used for predicting the binding affinities of various ligands. All docking experiments conducted herein were performed with the default parameters with AutoDock Vina on a MacOS (Big Sur) with an Intel Core i7 processor (2.6 GHZ) and 16 GB of RAM. Different docking runs finished at different times and the run time was not the limiting step (only a few minutes).

Intermediary steps, such as pdbqt files for protein and ligands preparation and grid box creation were completed using AutoDock Tools (ADT). AutoGrid was used for the preparation of the grid map using a grid box. The grid size was set to 45 Å×45 Å×45 Å with grid spacing of 1 Å and grid center was designated at xyz co-ordinates (43, 16, 96). AutoDock Vina was employed for docking using protein and ligand information along with grid box properties in the configuration file. During the docking procedure, the protein was considered as rigid and the ligand (polyol or fragments) was flexible. The structure with the top binding score represented the structure with the most favorable free energy of binding.

The 2D (two dimensional) structures of the ligand-protein complex was generated using LigPlot+ v. 2.2.

Formation of CD4-gp120 Complex

Immunoprecipitation studies conducted in the presence or absence of the linseed oil-derived polyol were performed to evaluate the impact of the polyol on the formation of the CD4-gp120 complex. A commercially available immunoprecipitation kit consisting of protein G-coated agarose beads (Invitrogen) was used, and immunoprecipitations were conducted according to the manufacturer's protocol. Briefly, the gp120 antibody (5 μg, Sigma-Aldrich) was bound to the protein G-coated agarose beads (50 μl) by placing the antibody and protein G agarose beads in 1.5 ml Eppendorf centrifuge tubes and incubated at room temperature for 10 minutes with rotation. The tubes were placed on the magnet (Life Technologies) and the supernatant was removed. The antigen consisted of recombinant gp120 (5 μg, Sigma-Aldrich), and CD4 (5 μg, R&D Systems) proteins were mixed with increasing amounts of the polyol (i.e., no polyol, 0.2%, 0.02%, and 0.002%) in the 1.5 ml tubes and incubated for 20 minutes at room temperature with rotation. For these experiments, gp120 was added to the tubes first, followed by the polyol, and then finally CD4 recombinant protein. Following incubation, the antibody-antigen complex mixture was placed on the magnet and the supernatant collected and stored. Laemmli sample buffer (50 μl, Bio-Rad) was added to elute the antibody-antigen complexes from the protein G beads. The samples were heated for 5 minutes at 95° C., then placed on the magnet, the supernatants were collected and analyzed via western blot. The converse combination in which CD4 protein was added first followed by the polyol and then gp120 recombinant was also performed.

Western Blot Analysis

A standard western blot technique was used to evaluate the impact of the polyol on CD4-gp120 complex formation. The supernatants described above were run on SDS/PAGE pre-cast gels (AnyKD or 12%, Bio-Rad) and transferred to a PVDF nitrocellulose membrane according to standard protocols. Briefly, SDS/PAGE running buffer was prepared and added to Bio-Rad precast gels placed in the Bio-Rad Tetra gel assembly. The antibody-antigen supernatants in Laemmli buffer (50 μl) were loaded on to the gels, and an electric voltage (100 V) was applied for 1 hour. After 1 hour the gel was removed from the pre-cast container, placed in western blot casing as described in the Bio-Rad Western blot protocol, and voltage was applied (100 V) for 1 hour to transfer the proteins from the gel to the PVDF nitrocellulose. Following the transfer, the PVDF nitrocellulose membrane was blocked for 1 hour with a 5% Milk powder solution (Blotto) then probed with either gp120 or CD4 monoclonal antibodies (in 1% Blotto) overnight at 4° C. The membranes were washed in Tris Buffered saline with 0.1% Tween-20 (TBS-T) for 6 five-minute intervals. After washing, the membrane was probed with secondary antibodies (goat-anti-mouse-HRP or goat-anti-rabbit-HRP) diluted 1:100,000 in 1% Blotto for 1 hour at room temperature with shaking. The membrane was washed as described above. Protein bands on the membrane were detected by chemiluminescence (Femto, ThermoFisher) and imaged on X-ray film (ThermoFisher). The blotted protein was quantified using the Image J software to measure the density, and the values were normalized to an untreated sample.

EXAMPLES

Following are Examples which are offered by way of illustration and are not intended to limit the invention. Various modifications or changes in light thereof will be suggested to persons skilled in the art and are to be included within the spirit and purview of this application. Unless otherwise stated, these Examples utilized the methods, techniques, and materials as described in Materials and Methods above and known to those skilled in the art.

Example 1—Molecular Docking Study of the Linseed Oil-Derived Polyol and Gp120

The human immunodeficiency virus (HIV) is known to infect the immune cells bearing the CD4 (cluster of differentiation 4) antigen receptor by binding to the CD4 with its envelope glycoprotein gp120 spikes. A molecular docking study was conducted to evaluate the anti-HIV effect of the linseed oil-derived polyol through binding to the HIV envelope glycoprotein gp120. The linseed oil-derived polyol of formula (I) was docked with gp120 and analyzed using AutoDock/Vina. The co-ordinates of NBD557 in complex with gp120 were taken from the crystal structure (PDB ID: 4DVR).

Figure 3:
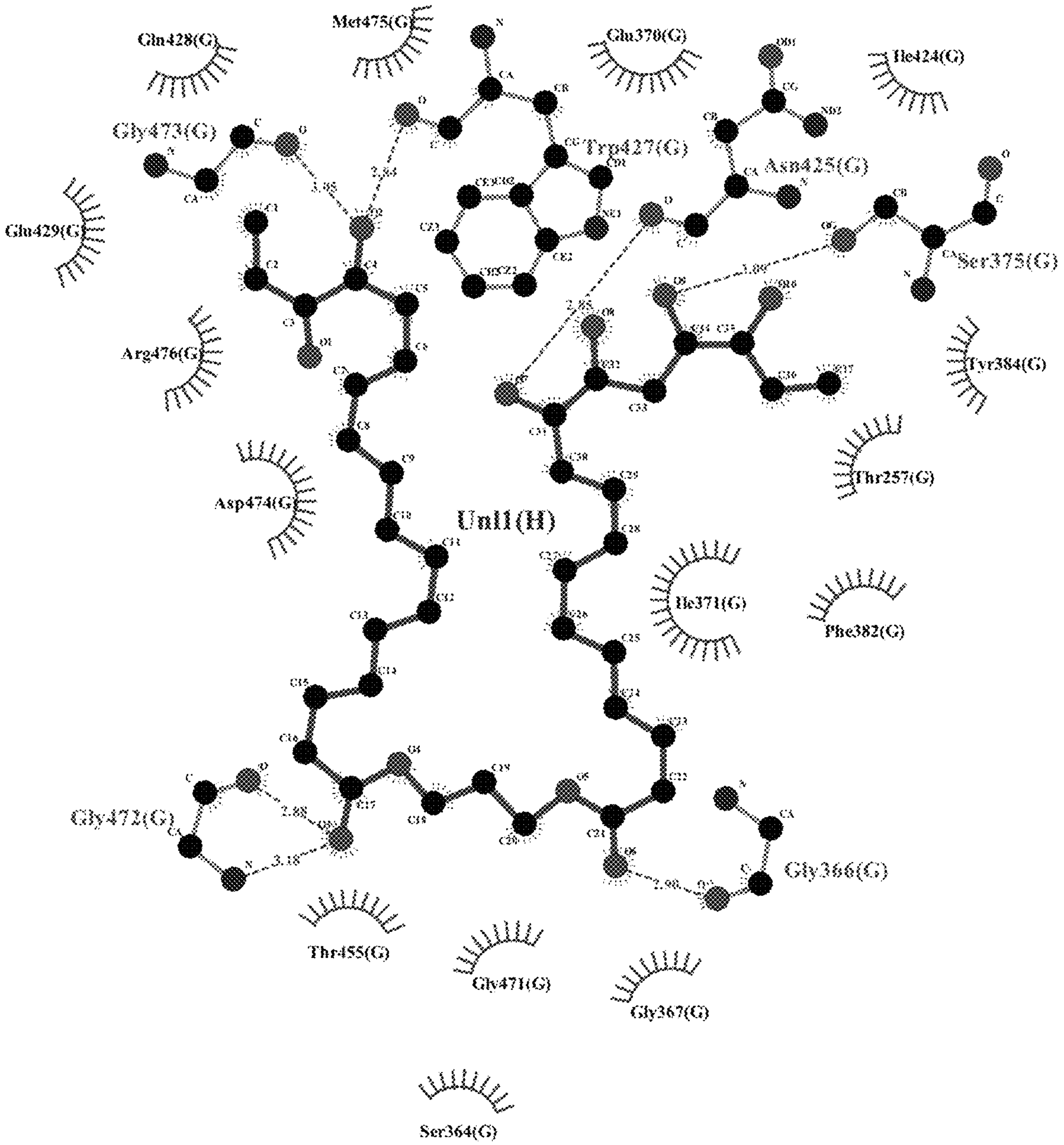
FIG. 3 provides a 2D (two-dimensional) interaction map of the complex of linseed oil-derived polyol and gp120.

As shown in FIG. 1, the results revealed that the linseed oil-derived polyol binds exclusively in the same gp120 cavity as NBD557. Because the small molecule NBD-557 mimics CD4 by binding to gp120 via Phe43, the results also demonstrate that the linseed oil-derived polyol and CD4 bind in the same gp120 cavity. The 2D interaction map generated by LigPlot+ further revealed that, during the interaction between the linseed oil-derived polyol and gp120, the hydroxyl groups on one of the fatty acid chains in the linseed oil-derived polyol make hydrogen-bonding interactions with Ser375 and Asn425 of gp120 (FIG. 3).

Example 2—Molecular Docking Study of the Linseed Oil-Derived Polyol and SARS-COV-2 Spike Protein A blind docking study was conducted using AutoDock/Vina to evaluate the interactions between the linseed oil-derived polyol of formula (I) and SARS-COV-2, the virus causing the coronavirus disease 2019 (COVID-19). SARS-COV-2 belongs to the family of Coronaviruses, whose genome is larger than other RNA viruses. SARS-COV-2 has the genome size of 29.9 kb. The SARS-COV-2 consists of four structural proteins (S, M, E, N) and 16 non-structural proteins. The results of the blind docking study showed that the linseed oil-derived polyol binds to three primary sites of the fully glycosylated SARS-COV-2 spike protein trimer structure (PDB ID: 6VXX)): 1) the top site being the cavity in the fusion core; 2) under the S1 subunit; and 3) near the receptor-binding domain (FIG. 4), indicating multiple potential sites where the polyol can bind and inhibit SARS-COV-2.

Example 3—Immunoprecipitation Assay with the Linseed Oil-Derived Polyol Alone The inhibitory effect of the linseed oil-derived polyol on the formation of CD4 and gp20 complex was evaluated with immunoprecipitation (IP). IP is a procedure which allows to observe the effect of protein binding in response to independent variables. IP relies on the use of SDS polyacrylamide gel electrophoresis to separate bound and unbound proteins by size. Here, soluble CD4 and gp120 were complexed in the presence or absence of the linseed oil-derived polyol. The concentration of the linseed oil-derived polyol varied from 0 to 1/1000, 1/100, 1/10, relative to the amount of the CD4-gp120 complex. IP was performed using Dynabeads™ Protein A Immunoprecipitation Kit (ThermoFisher, Catalog #10006D). A CD4 polyclonal antibody was used to pull down the CD4-gp120 complexes that were eluted according to the manufacturer's protocol. The eluates were subjected to a reduced SDS-PAGE (with beta-mercaptoethanol) and Western blot analysis. The blot was subsequently probed with a monoclonal gp120 antibody, and the bands were imaged with chemiluminescence.

Figure 5:
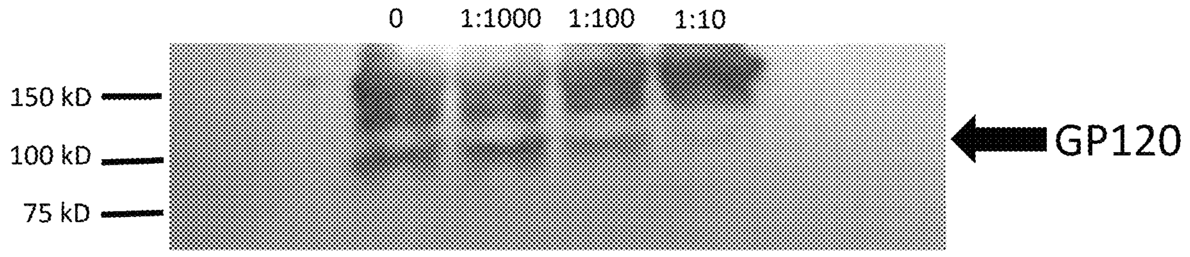
FIG. 5 provides results of Western blot analysis of immunoprecipitation evaluating the effect of the linseed oil-derived polyol on the formation of the CD4 and gp120 complex. The arrow indicates the bands for gp120.

The results in FIG. 5 demonstrate that increasing concentration of the linseed oil-derived polyol alone reduced the CD4-gp120 complex formation (see Lanes 1 through 4), as indicated by the bands of gp120. In FIG. 5, Lane 1 is a result of an assay with no Polyol. Lane 2 utilized the Polyol in the ratio of 1:1000 (Polyol: CD4-gp120). Lane 3 utilized the Polyol in the ratio of 1:100 (Polyol: CD4-gp120). Lane 4 utilized the Polyol in the ratio of 1:10 (Polyol: CD4-gp120).

Example 4—Molecular Docking Study of the Linseed Oil-Derived Polyol and Alditol Oxidase of *Streptomyces Coelicolor* Complexed with Mannitol A molecular docking study was conducted to evaluate the binding of the linseed oil-derived polyol to alditol oxidase. The polyol tail of linseed oil-derived polyol of formula (I) was docked with alditol oxidase of *Streptomyces coelicolor* complexed with mannitol (circled) (PDB ID: 2VFU) and analyzed using AutoDock/Vina.

The results in FIG. 6 demonstrate that the polyol tails of the linseed oil-derived polyol are similar to other sugar alcohol molecules such as mannitol, sorbitol, and xylitol, affecting the dehydrogenase activities in the sugar alcohol metabolism of many bacterial species, including *Agrobacterium, Streptomyces, Pseudomonas* and *Staphylococcus.*

All patents, patent applications, provisional applications, and publications referred to or cited herein are incorporated by reference in their entirety, including all figures and tables, to the extent they are not inconsistent with the explicit teachings of this specification.

We claim:

1. A method for inhibiting viral replication of a retrovirus or a coronavirus in a host cell, comprising, after the infection of the host cell by the virus, administering to the host cell a vegetable oil-derived polyol.

2. The method of claim 1, the retrovirus being HIV.

3. The method of claim 1, the coronavirus being SARS-COV-1 or SARS-COV-2.

4. The method of claim 1, the vegetable oil-derived polyol not being part of a hydrogel nanoparticle or microparticle.

5. The method of claim 1, the vegetable oil-derived polyol being a polyol derived from linseed oil.

6. The method of claim 5, the polyol derived from linseed oil comprising a compound of the formula (I):

(I)

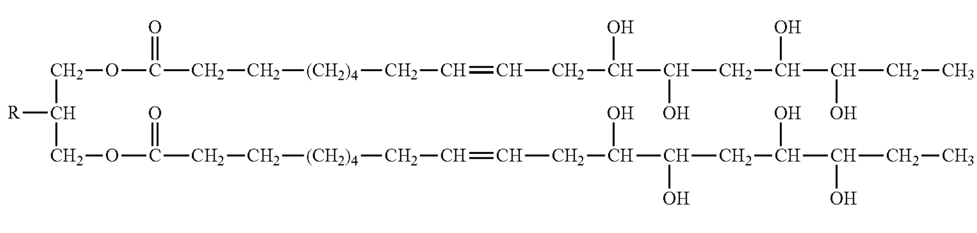

R being:

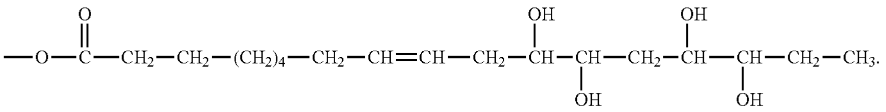

7. The method of claim 1, comprising administering to the host cell the vegetable oil-derived polyol in an effective amount at a concentration from 0.1 μg/ml to 500 μg/ml.

8. The method of claim 1, comprising administering to the host cell the vegetable oil-derived polyol alone.

9. A method for treating a retrovirus or a coronavirus infection in a subject, the method comprising administering to the subject an effective amount of a composition comprising a vegetable oil-derived polyol, which optionally, is complexed, aggregated, bonded, or associated with a second therapeutic agent.

10. The method of claim 9, the vegetable oil-derived polyol not being part of a hydrogel nanoparticle or microparticle.

11. The method of claim 9, the vegetable oil-derived polyol being a polyol derived from linseed oil comprising a compound of the formula (I)

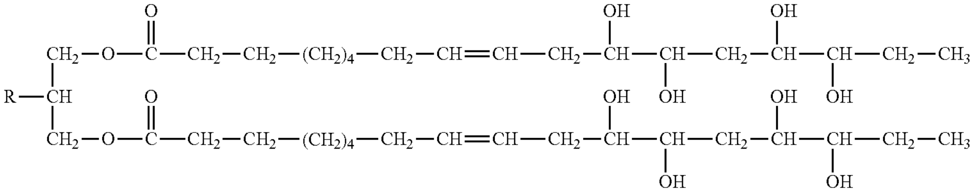

R being:

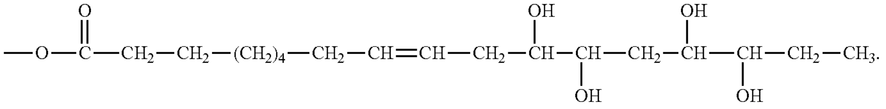

12. The method of claim 9, the administration being oral, topical, rectal, bronchial, nasal, topical, buccal, sub-lingual, transdermal, vaginal, intramuscular, intraperitoneal, intravenous, intra-arterial, subcutaneous, intracerebral, or intraocular administration.

13. The method of claim 9, the vegetable oil-derived polyol being a polyol derived from linseed oil.

* * * * *